United States Patent
Honarvar et al.

(10) Patent No.: US 11,672,503 B2
(45) Date of Patent: Jun. 13, 2023

(54) SYSTEMS AND METHODS FOR DETECTING TISSUE AND SHEAR WAVES WITHIN THE TISSUE

(71) Applicant: Sonic Incytes Medical Corp., Vancouver (CA)

(72) Inventors: Mohammad Honarvar, Richmond (CA); Caitlin Marie Schneider, Vancouver (CA); Julio Raul Lobo, Vancouver (CA); Brian Peter Stachniak, Delta (CA)

(73) Assignee: Sonic Incytes Medical Corp., Vancouver (CA)

( * ) Notice: Subject to any disclaimer, the term of this patent is extended or adjusted under 35 U.S.C. 154(b) by 0 days.

(21) Appl. No.: 17/820,802

(22) Filed: Aug. 18, 2022

(65) Prior Publication Data
US 2023/0054588 A1  Feb. 23, 2023

Related U.S. Application Data

(60) Provisional application No. 63/260,480, filed on Aug. 20, 2021.

(51) Int. Cl.
*A61B 8/00* (2006.01)
*A61B 8/08* (2006.01)
(Continued)

(52) U.S. Cl.
CPC .............. *A61B 8/085* (2013.01); *A61B 8/463* (2013.01); *A61B 8/485* (2013.01); *A61B 8/5223* (2013.01);
(Continued)

(58) Field of Classification Search
CPC combination set(s) only.
See application file for complete search history.

(56) References Cited

U.S. PATENT DOCUMENTS

| 4,621,645 A | 11/1986 | Flax |
| 10,667,791 B2 | 6/2020 | Baghani et al. |
| (Continued) | | |

FOREIGN PATENT DOCUMENTS

| KR | 102144672 B1 | 8/2020 |
| WO | 2018000103 A1 | 1/2018 |
| (Continued) | | |

OTHER PUBLICATIONS

Baghani, A. et al., "Real-time quantitative elasticity imaging of deep tissue using free-hand conventional ultrasound", Medical Image Computing and Computer-Assisted Intervention—MICCAI 2012, 2012, pp. 617-624.

(Continued)

*Primary Examiner* — Joel F Brutus
(74) *Attorney, Agent, or Firm* — Oyen Wiggs Green & Mutala LLP

(57) ABSTRACT

Example embodiments of the described technology provide systems and methods for ultrasound imaging. An example method may detect the presence of shear waves within a tissue region of a patient. The method may comprise exciting the tissue region of the patient with one or more exciters to induce propagation of shear waves within the tissue. A plurality of ultrasound images of the tissue may be acquired. A first image mask indicating which pixels of the acquired images represent a desired tissue type using a first trained machine learning model may be generated. The method may also comprise generating a second image mask indicating which pixels of the acquired images represent shear waves using a second trained machine learning model.

23 Claims, 8 Drawing Sheets

(51) Int. Cl.
*G06T 7/174* (2017.01)
*G06T 7/11* (2017.01)

(52) U.S. Cl.
CPC ............. *G06T 7/11* (2017.01); *G06T 7/174* (2017.01); *G06T 2207/10132* (2013.01); *G06T 2207/20081* (2013.01); *G06T 2207/20084* (2013.01); *G06T 2207/30056* (2013.01)

(56) References Cited

U.S. PATENT DOCUMENTS

| | | | |
|---|---|---|---|
| 2012/0108968 A1* | 5/2012 | Freiburger | A61B 8/5223 600/443 |
| 2017/0020486 A1 | 1/2017 | Salcudean et al. | |
| 2019/0076126 A1 | 3/2019 | Greenleaf et al. | |
| 2019/0083067 A1* | 3/2019 | Kim | G01S 15/8979 |
| 2019/0148011 A1* | 5/2019 | Rao | A61B 8/54 600/437 |
| 2021/0022715 A1 | 1/2021 | Brattain et al. | |

FOREIGN PATENT DOCUMENTS

| | | |
|---|---|---|
| WO | 2020048875 A1 | 3/2020 |
| WO | 2020254159 A1 | 12/2020 |

OTHER PUBLICATIONS

Kuc, R., "Clinical application of an ultrasound attenuation coefficient estimation technique for liver pathology characterization", IEEE Transactions on Biomedical Engineering, (6), 1980, pp. 312-319.

Ophir, J. et al., "Attenuation estimation in reflection: progress and prospects", Ultrasonic Imaging, 6(4), 1984, pp. 349-395.

Ronneberger, O. et al., "U-Net: Convolutional Networks for Biomedical Image Segmentation", 2015, arXiv:1505.04597.

Long, J. et al., "Fully convolutional networks for semantic segmentation", Proceedings of the IEEE conference on computer vision and pattern recognition, 2015.

* cited by examiner

SYSTEMS AND METHODS FOR DETECTING TISSUE AND SHEAR WAVES WITHIN THE TISSUE

CROSS-REFERENCE TO RELATED APPLICATION

This application claims priority from U.S. application No. 63/260,480 filed 20 Aug. 2021 and entitled SYSTEMS AND METHODS FOR DETECTING TISSUE AND SHEAR WAVES WITHIN THE TISSUE which is hereby incorporated herein by reference for all purposes. For purposes of the United States of America, this application claims the benefit under 35 U.S.C. § 119 of U.S. application No. 63/260,480 filed 20 Aug. 2021 and entitled SYSTEMS AND METHODS FOR DETECTING TISSUE AND SHEAR WAVES WITHIN THE TISSUE.

FIELD

The present disclosure relates to ultrasound systems and methods. Some embodiments provide systems and methods useful for detecting specific tissue and/or shear waves within the tissue.

BACKGROUND

Ultrasound is commonly used to image tissue. To acquire image data, ultrasound pulses are transmitted into the tissue and reflected signals (i.e. "echoes") are received back from the tissue. Properties of the imaged tissue can be deduced from the received echo signals.

For example, the liver performs several vital functions in the human body such as filtering blood from the digestive tract, detoxifying blood and metabolizing biochemical compounds (carbohydrates, proteins, fats, etc.). A patient suffering from liver disease has a liver which cannot properly perform these functions. As liver disease progresses, the liver's ability to perform these functions is reduced.

Progress of liver disease may be assessed by measuring one or more characteristics of the liver. Such characteristics may be determined from acquired image data of the liver.

Tissue elasticity may be measured by acquiring ultrasound elastography data as described, for example, in: A. Baghani et al., "Real-time quantitative elasticity imaging of deep tissue using free-hand conventional ultrasound" in Medical Image Computing and Computer-Assisted Intervention—MICCAI 2012, 2012, pp. 617-624 and in U.S. Pat. No. 10,667,791 to BAGHANI et al. and entitled ELASTOGRAPHY USING ULTRASOUND IMAGING OF A THIN VOLUME.

The attenuation of ultrasound signals in tissue may be measured by acquiring ultrasound attenuation data as described, for example, in: Kuc, R., 1980, "Clinical application of an ultrasound attenuation coefficient estimation technique for liver pathology characterization", IEEE Transactions on Biomedical Engineering, (6), pp.312-319; Ophir, J. et al., 1984, "Attenuation estimation in reflection: progress and prospects" Ultrasonic Imaging, 6(4), pp.349-395; and U.S. Pat. No. 4,621,645 to Flax and entitled METHOD OF ESTIMATING TISSUE ATTENUATION USING WIDEBAND ULTRASONIC PULSE AND APPARATUS FOR USE THEREIN.

There is a need for improved systems and methods for ultrasound imaging. There is also a need for improved systems and methods for assessing the health of tissues such as liver tissues.

SUMMARY

This invention has a number of aspects. These include, without limitation:
systems and methods for imaging tissue of a patient;
systems and methods for identifying and/or detecting tissue (e.g. organs such as the liver) in image data;
systems and methods for measuring liver health metrics using elastography;
systems and methods for guiding an operator to obtain good quality liver health metrics;
systems and methods for recognizing shear waves in tissue of a patient;
systems and methods for verifying the presence of shear waves in tissue of a patient;
systems and methods for assessing quality of acquired image data;
systems and methods for assessing quality of shear waves propagating through tissue of a patient;
systems and methods for determining one or more quality metrics of acquired data;
systems and methods for displaying one or more quality metrics to an operator.

One aspect of the invention provides a method for detecting presence of shear waves within a tissue region of a patient. The method may comprise exciting the tissue region of the patient with one or more exciters to induce propagation of shear waves within the tissue region. The method may also comprise acquiring a plurality of ultrasound images of the tissue region. The method may also comprise generating a first image mask indicating which pixels of the acquired plurality of ultrasound images represent a desired tissue using a first trained machine learning model. The method may also comprise generating a second image mask indicating which pixels of the acquired plurality of ultrasound images represent shear waves using a second trained machine learning model.

In some embodiments the method comprises generating the first image mask and the second image mask concurrently.

In some embodiments the first trained machine learning model is trained to detect the desired tissue based on boundaries of the tissue.

In some embodiments the first trained machine learning model is configured to segment pixels of the plurality of ultrasound images of the tissue into at least a first group corresponding to the desired tissue and a second group corresponding to tissue other than the desired tissue.

In some embodiments the first trained machine learning model is configured to segment pixels of the plurality of ultrasound images of the tissue into at least a first group corresponding to a first tissue type, a second group corresponding to a second tissue type different from the first tissue type and a third group corresponding to tissue other than the first and second tissue types.

In some embodiments the first trained machine learning model comprises a convolutional neural network.

In some embodiments the first trained machine learning model comprises a U-Net convolutional neural network.

In some embodiments the first mask comprises a binary mask.

In some embodiments the first mask comprises pixel values representing a probability that the corresponding pixels of the acquired ultrasound images represent the desired tissue.

In some embodiments the second trained machine learning model comprises a convolutional neural network.

In some embodiments the second trained machine learning model comprises a U-Net convolutional neural network.

In some embodiments the second trained machine learning model receives as input shear wave data corresponding to a shear wave propagating through the desired tissue region and image data of the desired tissue region.

In some embodiments the second trained machine learning model comprises a first branch configured to receive as input the shear wave data corresponding to the shear wave and a second branch configured to receive as input the image data.

In some embodiments the shear wave data corresponding to the shear wave comprises at least one of: different states of the shear wave in time; a real part and an imaginary part of a phasor representing the shear wave; and a magnitude and phase of the phasor.

In some embodiments each branch comprises a down-sampling path and an up-sampling path.

In some embodiments the down-sampling path and the up-sampling path of a corresponding branch have an equal depth.

In some embodiments the down-sampling path and the up-sampling path of the corresponding branch each have a depth of 4.

In some embodiments the method comprises generating a quality mask of the acquired ultrasound image data based at least partially on the first mask and the second mask. The quality mask may comprise pixel values representing a quality metric of the corresponding pixels of the acquired ultrasound images.

In some embodiments generating the quality mask comprises combining the first and second masks together.

In some embodiments the quality mask indicates at least one of ultrasound signal-to-noise ratio, ability to track tissue displacements, fitting of tissue displacements to known frequencies of input vibrations, shear wave presence and identification of tissue type.

In some embodiments the method comprises applying the quality mask to input ultrasound data to determine which pixels of the input data to use for downstream processing or to label the input data.

In some embodiments the method comprises performing a pixel wise logical AND operation to combine the first mask and the second mask to yield the quality mask.

In some embodiments the method comprises cropping the quality mask to a fixed two-dimensional or three-dimensional region of interest.

In some embodiments cropping the quality mask comprises maximizing within a crop region the number of pixels which comprise both the desired tissue and good shear waves.

In some embodiments the method comprises dynamically varying the region of interest that is displayed in real time as image data is updated.

In some embodiments the method comprises displaying over the ultrasound image data the first mask in a first colour, the second mask in a second colour different from the first colour and the quality mask in a third colour different from the first and second colours.

Another aspect of the invention provides a method for assessing quality of acquired ultrasound imaging data of a patient. The method may comprise exciting a tissue region of the patient with one or more exciters to induce propagation of shear waves within the tissue region. The method may also comprise acquiring a plurality of ultrasound images of the tissue region. The method may also comprise displaying a quality metric representing the quality of the ultrasound images. The quality metric of the ultrasound images may at least partially be based on:
 a number of pixels of the ultrasound images which represent a desired tissue, the number of pixels representing the desired tissue determined using a first machine learning model trained to detect pixels of the desired tissue; and
 a number of pixels of the ultrasound images which represent shear waves traveling through the desired tissue, the number of pixels representing shear waves determined using a second machine learning model trained to detect pixels corresponding to shear waves.

Another aspect of the invention provides a method for detecting presence of shear waves within a tissue of interest in a tissue region of a patient. The method may comprise exciting the tissue region of the patient with one or more exciters to induce propagation of shear waves within the tissue region by vibrating the tissue region with the one or more exciters. The method may also comprise while exciting the tissue region, acquiring a plurality of ultrasound images of the tissue region with an ultrasonic transducer acoustically coupled to the patient. The method may also comprise processing the acquired plurality of ultrasound images to determine characteristics of the shear waves. The method may also comprise displaying at least some of the acquired plurality of ultrasound images on a display. The method may also comprise displaying a visual indicator representing a measure of how well the acquired plurality of ultrasound images capture the tissue of interest within the tissue region and a quality measure of shear waves traveling through the tissue of interest.

The visual indicator may be determined at least partially from:
 a first image mask indicating which pixels of the acquired plurality of ultrasound images represent the tissue of interest, the first image mask generated by inputting one or more of the acquired plurality of ultrasound images into a first machine learning model trained to identify the tissue of interest within one or more input ultrasound images; and
 a second image mask indicating which pixels of the acquired plurality of ultrasound images represent shear waves usable to determine an elasticity property of the tissue of interest, the second mask generated by inputting the acquired plurality of ultrasound images and shear wave data corresponding to the shear waves travelling through the tissue of interest into a second machine learning model trained to identify shear waves usable to determine the elasticity property of the tissue of interest.

In some embodiments the method may comprise any of the features or any combination of features described herein.

Another aspect of the invention provides a system for imaging tissue of a patient. The system may comprise at least one exciter controllable to induce propagation of shear waves within tissue of the patient. The system may also comprise an ultrasound imaging system operable to acquire ultrasound imaging data of a tissue region of the patient. The system may also comprise a controller configured to control the at least one exciter and the ultrasound imaging system. The controller may comprise a first trained machine learning model to generate a first image mask indicating which pixels of acquired images represent a desired tissue type. The method may also comprise a second trained machine learning model to generate a second image mask indicating which pixels of the acquired images represent shear waves.

In some embodiments the system is configured to perform a method described herein.

It is emphasized that the invention relates to all combinations of the above features, even if these are recited in different claims.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One example aspect of the technology described herein provides systems and methods for ultrasound imaging. The systems and methods may detect the presence of a tissue type (or tissue types) within acquired ultrasound images, detect the presence of shear waves in acquired ultrasound images, assess quality of acquired ultrasound images (e.g. based on a desired tissue (or tissues) being detected in the acquired ultrasound images and/or the presence of shear waves being detected in the acquired ultrasound images), etc.

In some embodiments a tissue region of a patient is excited with one or more exciters to induce propagation of shear waves within the tissue region. A plurality of ultrasound images of the tissue region may be acquired. A first image mask indicating which pixels of the acquired images represent a desired tissue type may be generated using a first trained machine learning model. A second image mask indicating which pixels of the acquired images represent shear waves may also be generated using a second trained machine learning model. A quality metric representing a quality of the acquired ultrasound images may be determined based on the first mask and/or the second mask.

Figure 1:
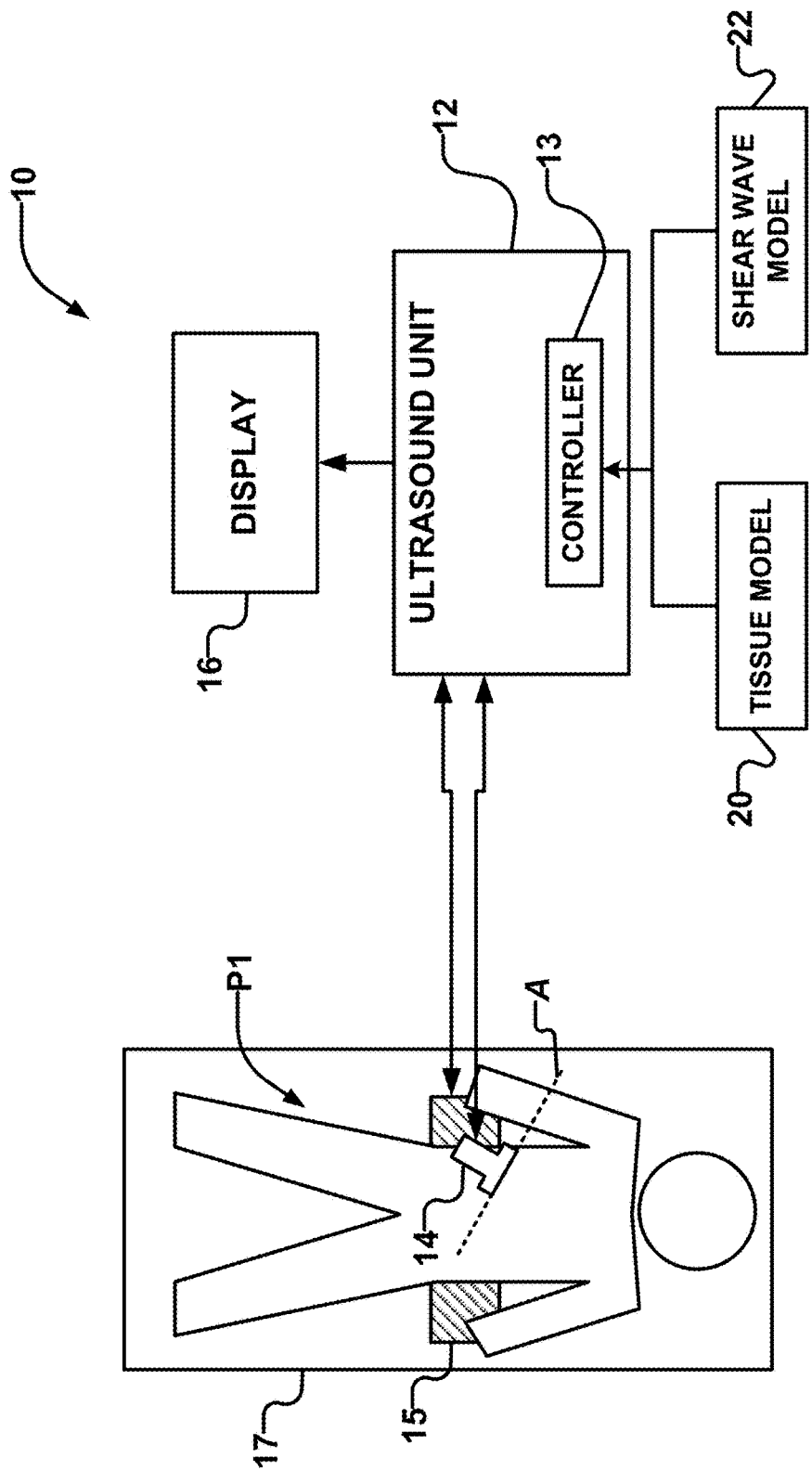
FIG. 1 is a schematic illustration of an ultrasound system according to an example embodiment of the present technology.

FIG. 1 schematically shows an example ultrasound system 10 operable to concurrently provide a measure of elastography and attenuation properties of an imaged tissue region of patient P1.

System 10 comprises an ultrasound unit 12 having a controller 13. An ultrasound transducer 14 is coupled to ultrasound unit 12. Transducer 14 is positioned adjacent to the skin of a patient P1 proximate to a region or volume of tissue that is to be imaged to acoustically couple transducer 14 to patient P1. Transducer 14 may, for example, comprise a 1D or 2D array of transducer elements. Transducer 14 may have a linear or non-linear transducer face.

Ultrasound unit 12 is operative to obtain ultrasound images of the region or volume of tissue of interest (e.g. all or a portion of a person's liver). The basic principles of ultrasound imaging are well known and are not described herein. Ultrasound unit 12 may, for example, comprise commercially available ultrasound imaging components. Ultrasound unit 12 may be operative to obtain three-dimensional (3D) images of the region or volume of tissue of interest.

Images of a three-dimensional (3D) volume of tissue may be obtained, for example, by using a two-dimensional (2D) matrix transducer array or by moving a one-dimensional (1D) transducer array. In some embodiments beam steering of a 2D transducer array is used to obtain 3D images of a 3D volume of tissue. A transducer 14 may be moved relative to patient P1 to acquire a larger volume of ultrasound data. For example, transducer 14 may be pivoted angularly about an axis A and/or translated along the skin of patient P1.

In some embodiments transducer 14 is positioned manually relative to patient P1 by an operator of system 10. In some embodiments transducer 14 is positioned and/or moved by a mechanical system. In some embodiments a robotic system is controlled to position transducer 14.

To measure elastography properties of the imaged tissue, ultrasound unit 12 tracks movements of the imaged tissue in response to shear waves which propagate through the tissue. The shear waves may be induced into the tissue by one or more exciters 15. An exciter 15 is a device which can generate shear waves that may propagate through tissues of patient P1. For example, exciter 15 may comprise: an electromagnetically driven vibration transducer, an unbalanced rotor, a vibrating table, or the like. For example, exciter(s) 15 may be constructed as described in international patent publication WO 2018/000103 A1 which is hereby incorporated herein by reference for all purposes.

An exciter 15 may be positioned proximate to the region of tissue to be imaged. For example, exciter 15 may comprise a vibrating pad or plate which is positioned underneath patient P1 on a bed 17. Preferably the pad or plate is sufficiently stiff to induce shear waves within patient P1. In some embodiments, exciter 15 is integrated into transducer 14.

Controller 13 controls transducer 14 and exciter 15 to acquire ultrasound imaging data according to a desired imaging plan. Controller 13 may also receive and process received echo signals from transducer 14. If system 10 comprises a positioning system (e.g. a mechanical system or robotic system as described above) that is operative to control the position of transducer 14, controller 13 may control the positioning system to vary the position of transducer 14.

System 10 may record positions of transducer 14 as ultrasound imaging data is acquired. In some embodiments controller 13 controls the recording of the positions of transducer 14. The recorded position data may be used in volume reconstruction of the acquired imaging data (e.g. rendering a tissue volume from the acquired imaging data). In some embodiments a position is recorded for every acquired image. In some embodiments a position is recorded every time the position of transducer 14 changes by more than a threshold amount. In some embodiments the position data comprises one or more angles of transducer 14 relative to patient P1, positions of transducer 14 relative to patient P1 and/or the like.

In some embodiments system 10 comprises a display 16. Display 16 may display information such as:
- acquired imaging data;
- a subset of acquired imaging data (e.g. an enlarged region of interest);
- a quality of acquired imaging data (e.g. based on a signal to noise ratio);
- settings of system 10 (e.g. set parameters (frequency, amplitude, etc.) of pulse signals);
- a desired imaging plan;
- one or more measures of quality of the acquired data;
- one or more measures of health of the imaged tissue;
- patient particulars;
- etc.

In some embodiments system 10 (e.g. controller 13) assesses a quality of the ultrasound images being acquired and/or the shear waves which are propagating through the tissue. In some embodiments system 10 displays a visual indicator for an operator indicating whether imaging data of a sufficiently high enough quality is being acquired (e.g. there are enough pixels in an image which represent a desired tissue type (e.g. the liver) and/or enough pixels in an image which represent good shear waves and/or there are enough pixels to represent a sufficiently large volume of a desired tissue). The visual indicator may be one or more of a numerical indicator, an image overlay or mask indicating desirable pixels, etc. The visual indicator may indicate the magnitude of a quality metric determined as described elsewhere herein. In some embodiments the numerical indicator is displayed on a graphical user interface (GUI) of system 10. In some embodiments the numerical indicator is displayed as a coloured bar (e.g. different positions along the bar or colours of the bar correspond to different qualities of the acquired ultrasound images).

Detection of Tissue Type(s)

In some embodiments system 10 autonomously (or partially autonomously) detects the presence of a desired type of tissue (e.g. liver tissue) in acquired image data. System 10 may, for example, detect boundaries between different portions of an acquired image (e.g. between portions of the image representing a desired tissue type such as the liver and portions of the image which do not represent the desired tissue type), characterizing features of the desired tissue type (e.g. specific blood vessels which are found in the desired tissue type, shapes of lobes or other volumes which are unique to the desired tissue type, number of lobes or other volumes, etc.) and/or the like.

A visual indicator such as a colour image mask or outline overlaying the detected tissue type may be displayed (e.g. on display 16) for an operator of system 10. Additionally, or alternatively, a numerical indicator may be displayed for the operator. The numerical indicator may, for example, represent a percentage of pixels in an image which correspond to the desired tissue type. The numerical indicator may further indicate that a desired threshold has been reached (e.g. that the acquired imaging data comprises a sufficient number of pixels corresponding to the desired tissue type).

System 10 may, for example, comprise a machine learning model 20 which has been trained to autonomously detect the desired type of tissue(s) (e.g. liver tissue). In some embodiments model 20 comprises a trained neural network. In some embodiments the trained neural network is a convolutional neural network. In some embodiments the convolutional neural network comprises a U-Net architecture (e.g. a U-Net architecture as developed by the Computer Science Department of the University of Freiburg in Germany which is described for example in: Ronneberger, Olaf; Fischer, Philipp; Brox, Thomas (2015). "U-Net: Convolutional Networks for Biomedical Image Segmentation". arXiv:1505.04597.).

Model 20 may, for example, exist on a data processor such as a commercially available graphics processing unit (GPU). The data processor may be configured to implement model 20 according to machine readable instructions that define the topology of model 20 and data that specifies values for weights used in model 20.

Model 20 may, for example, be trained to perform image segmentation of incoming images of tissue (e.g. incoming ultrasound B-mode images acquired from ultrasound signals acquired by transducer 14). The segmentation may, for example, identify a desired tissue type such as liver tissue. Model 20 may, for example, segment pixels of the incoming images into two groups. The pixels may be segmented into a first group corresponding to pixels which represent the desired tissue type (e.g. liver tissue) and a second group corresponding to pixels which do not represent the desired tissue type (e.g. non-liver pixels).

In some embodiments model 20 segments pixels of the incoming images into a plurality of groups representing different tissue types or ultrasound image features. For example, the pixels may be segmented into groups representing one or more of: liver tissue, kidney tissue, shadows (e.g. caused at least partially by bone tissue such as rib bones) and unlabeled pixels. In some embodiments the group corresponding to unlabeled pixels comprises pixels which are unimportant and/or not used for downstream processing.

As described above model 20 may output an image mask representing the pixels in which liver tissue was detected. In some embodiments the mask is a binary mask (e.g. '1' if the pixel corresponds to liver tissue and '0' if the pixel corresponds to non-liver tissue). In some embodiments the mask may at least partially be used to determine a quality metric of the incoming image data. For example, a quality of the mask may be determined based on the number of pixels corresponding to the specific tissue type (e.g. liver tissue) relative to a total number of pixels in the image (e.g. if 60 pixels out of 100 pixels correspond to the specific tissue type the quality of the incoming images and/or the generated mask may be 60%). Additionally, or alternatively, pixel values of the mask may represent a probability that the corresponding pixels represent the desired tissue type. Possible pixel values may, for example, be mapped to a likelihood ranging from 0% to 100%. For example, gray scale pixel values ranging from 0 to 255 may be mapped to a likelihood ranging from 0% to 100%.

As described elsewhere herein model 20 may receive two-dimensional B-mode ultrasound image data as input. Model 20 is not necessarily limited to B-mode ultrasound image data or ultrasound imaging data more generally. In some embodiments model 20 receives image data other than ultrasound image data such as MRI image data, CT image data, etc. In some embodiments the input image data is resized. In some embodiments the input image data is down-sampled. In some embodiments the input image data is down sampled to 512×512 pixels, 256×256 pixels, 128×128 pixels, 64×64 pixels, etc. Model 20 may output a mask representing pixels which have been identified as corresponding to the desired tissue type.

Figure 2:
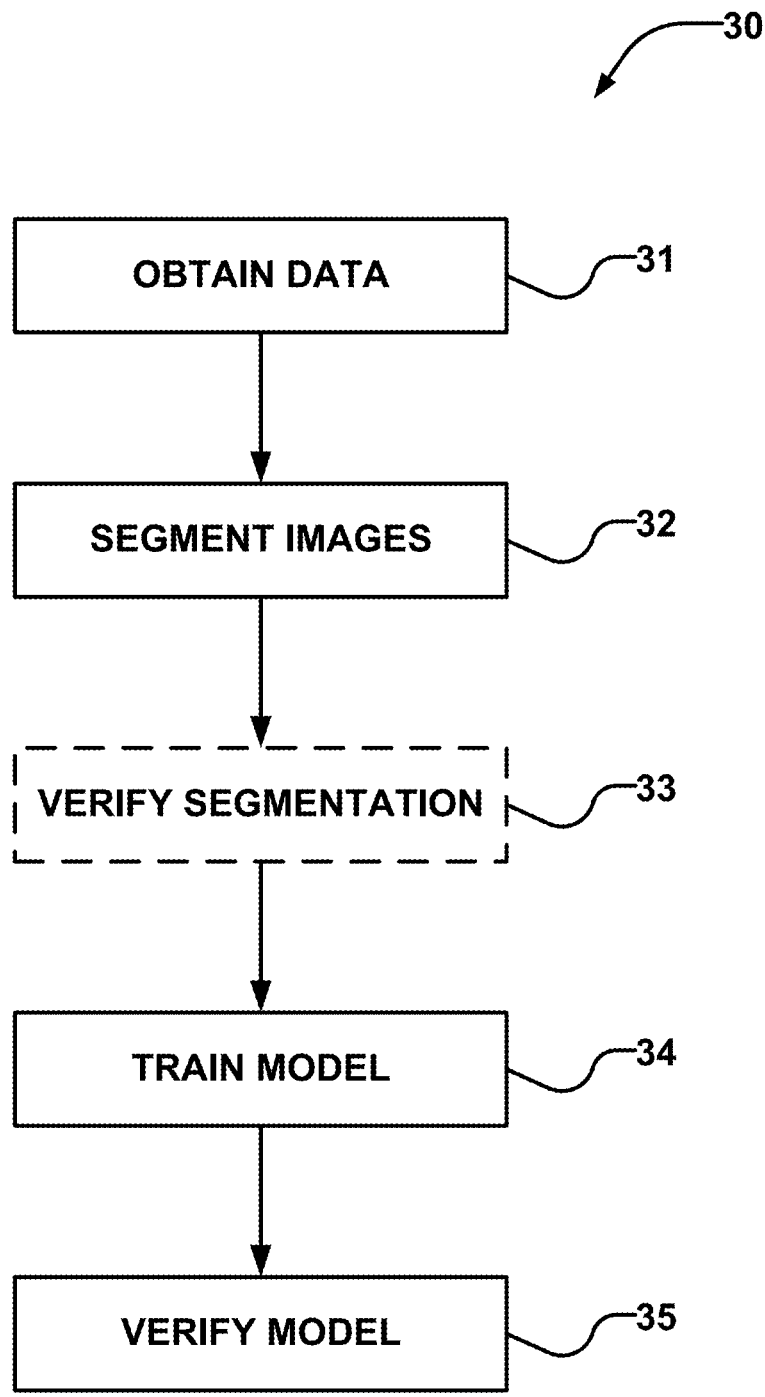
FIG. 2 is a block diagram of a method according to an example embodiment of the present technology.

FIG. 2 illustrates an example method 30 for training model 20.

In block 31 data for training model 20 is obtained. For example, the training data may comprise images that include the desired tissue type from both healthy patients and patients whose tissue of the desired type is at least partially diseased. For example, if liver data is being collected, liver images from healthy volunteers may be collected as well as from volunteers who have fatty liver disease, a hepatitis C (HCV) infection, increased levels of fibrosis, increased levels of steatosis and/or the like.

In one example case images of a total of 65 patients were taken. In such case 50-150 images (e.g. abdominal ultrasound images) per patient were collected.

In another example case images of a total of 198 patients were taken. In such case 50-150 images (e.g. abdominal ultrasound images) per patient were collected. Two different ultrasounds probes were used to increase diversity of the input data (e.g. 65 patients imaged with first ultrasound probe and 134 patients imaged with second ultrasound probe).

In block 32 the obtained training images are segmented. In some embodiments the images are manually segmented (e.g. by human experts). In some embodiments the images are at least partially segmented or sorted by software (e.g. by a software sorting program).

The performed segmentations are optionally verified in block 33. In some embodiments block 33 comprises verifying or checking the segmentation performed in block 32 for accuracy, consistency and/or the like. In some embodiments all segmented pixels are verified. In some embodiments a subset of pixels (e.g. about 5-20%) are verified. The subset of pixels to be verified may be randomly chosen.

In block 34 model 20 is trained using the segmented images. The training comprises iteratively setting coefficients (weights) of nodes in layers of the neural network of model 20. The segmented images are inputted into the network and the resulting output of model 20 is compared with the results of the manual segmentations. The coefficients are adjusted (e.g. by back propagation) and the training process is repeated until the error between the output of model 20 and the manual segmentations converges below a threshold amount.

In block 35 model 20 is verified. Typically a subset (e.g. about 5-20%) of the segmented images are set aside and not used during the training of block 34. The subset of segmented images is input into trained model 20 to check the accuracy of model 20 for segmenting images that it was not trained on, for example, to make sure that model 20 was not overfitted to the specific set of images used to train model 20. The segmentation performed by model 20 may be compared against a segmentation performed by a human expert to check the accuracy of model 20.

Figure 3:
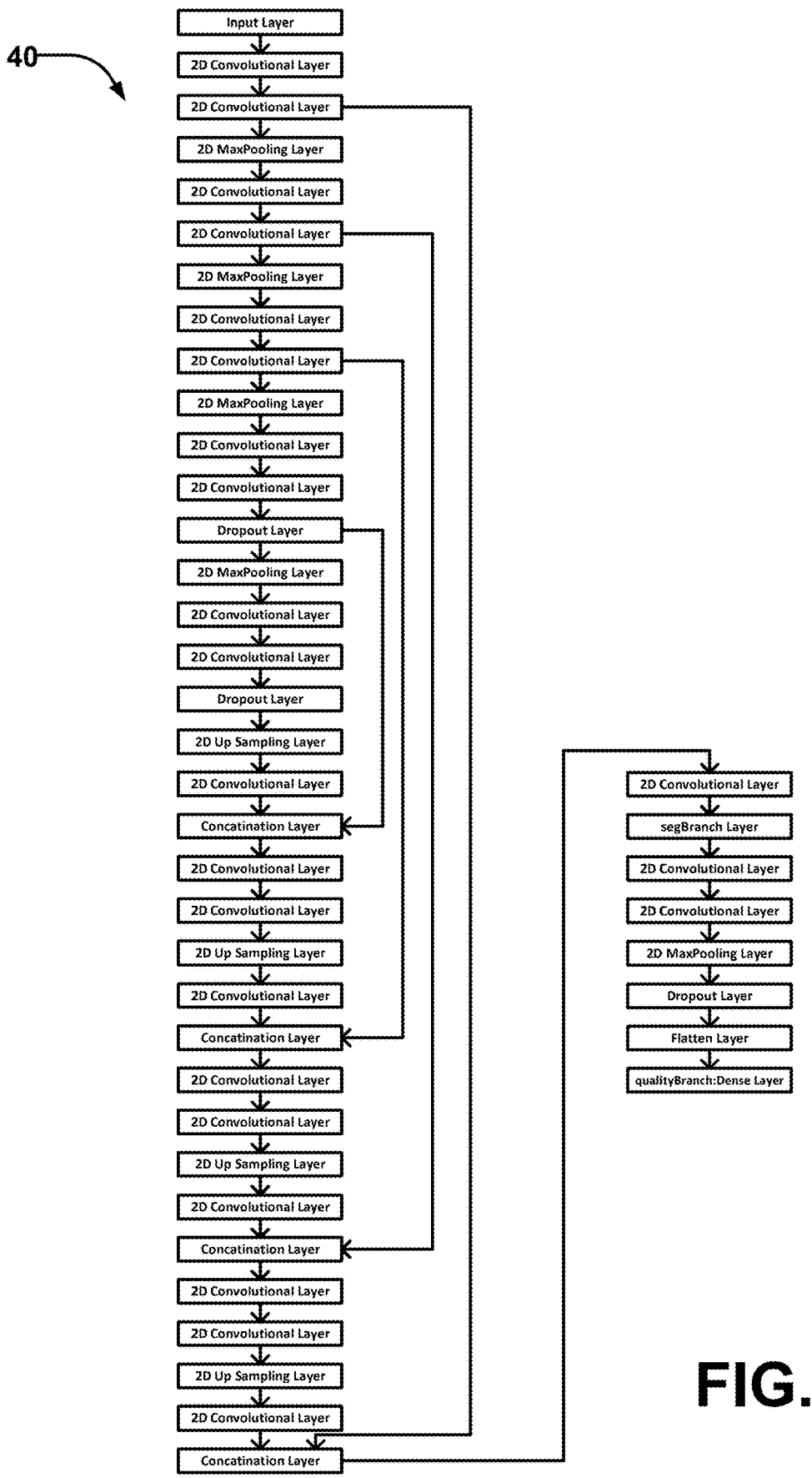
FIG. 3 is a block diagram of a machine learning model according to an example embodiment of the present technology.

FIG. 3 is a block diagram illustrating an example U-NET architecture 40 that may be used to implement machine learning model 20. Architecture 40 was implemented in Keras™ with a TensorFlow™ backend. As shown in FIG. 3, example architecture 40 comprises layers such as convolutional layers, max pooling layers, dropout layers, up sampling layers, concatenation layers, etc.

The example image size used to train model 20 comprising example architecture 40 was 256 by 256 pixels. There were about 3,000 training image samples. About 400 image samples were used for validation. In total model 20 comprised about 600,000 parameters. Cross entropy measuring next classification accuracy was used as an error metric. Both augmentation and dropout strategies were used to prevent overfitting.

Detection of Shear Wave Quality

Additionally, or alternatively, system 10 may determine a quality of measured shear waves propagating through a tissue region of patient P1 at any given time. System 10 may concurrently identify a desired tissue type (or types) such as liver tissue as well as determine the quality of the measured shear waves which propagate through the desired tissue type.

As described above the tissue region of patient P1 may be vibrated using one or more external exciters (e.g. exciters 15). Vibrating the tissue region with the one or more exciters generates shear waves which propagate throughout the tissue region. The generated shear waves may be tracked by acquiring ultrasound imaging data of the tissue region while the tissue region is being vibrated or excited. The acquired RF ultrasound data may be used to track the generated shear waves (or tissue displacements caused by the propagation of the shear waves through the tissue). In some embodiments tissue motion (or positions of the desired tissue type) is sampled in time for at least some points in space. In some embodiments tissue motion (or positions of the desired tissue type) is sampled in time for each point in space. The tracked tissue displacements may be fitted to a cosine function sampled in time (excitation frequency is known).

Displacement phasors may then be determined based on the cosine function. For example, a displacement phasor (P) may be represented as:

$$P=Ae^{i\theta}=A(\cos\theta+i\sin\theta)=P_r+iP_i$$

where A corresponds to the magnitude of the tissue displacement, $\theta$ corresponds to the phase and $P_r$ and $P_i$ correspond to the real and imaginary components respectively of phasor (P). The displacement phasors may be used to synchronize all the points in a region of interest and reveal any spatial waves. The spatial waves may be traveling shear waves, standing shear waves or compressional waves.

During a steady state harmonic vibration of the tissue, the wavelength of the shear waves is related to a shear modulus value of the tissue. It is therefore typically advantageous to have good quality shear wave measurements in order to allow for reliable shear modulus reconstruction of the tissue.

Several factors may impact the quality of shear waves which are detected by system 10. For example, in the context of liver tissue imaging, one or more of the following factors may impact shear wave quality (non-limiting):

- a patient with a high body mass index (e.g. larger distance between outer skin layer and surface of the liver attenuates ultrasound signals more (compared to a smaller distance) thereby resulting in a lower signal-to-noise ratio (SNR));
- reverberation artifact (e.g. pointwise metrics of the shear wave may deceptively represent the measured phasor as a true shear wave but one can only tell if measured phasor is a true shear wave by assessing the phasor in space over a time period to tell whether the phasor corresponds to a true shear wave (a travelling wave));
- probe motion introducing artifacts;
- presence of strong (e.g. higher amplitude) compressional waves compared to lower amplitude shear waves;
- patient motion (e.g. inability to hold breath for a desired amount of time);
- etc.

For liver tissue, good shear waves typically have the following properties (non-limiting):

shear waves appear as travelling waves (e.g. waves move in space over time) as distinct from compressional waves and other motion tracking artifacts which typically appear as standing waves;

as an excitation frequency of the one or more exciters increases the wavelength of the good shear wave should decrease;

good shear waves change smoothly in space (e.g. there should not be sharp changes in the wave pattern);

a direction of the good shear waves is typically from the ribcage to the inside of the liver; and/or a wavelength of the shear waves should be within an expected range for liver tissue (for example, a single frequency exciter operating at 50 Hz should generate shear waves with wavelengths of approximately 2.6-5.2 cm for liver stiffness in the range of about 5 kPA to 20 kPa);

etc.

In some embodiments system 10 comprises a machine learning model 22 which has been trained to detect quality of shear waves propagating through a desired tissue region (e.g. liver tissue). In some embodiments model 22 comprises a trained neural network. In some embodiments model 22 comprises a trained convolutional neural network. In some embodiments model 22 comprises a U-Net based convolution neural network.

Model 22 may, for example, exist on a data processor such as a commercially available graphics processing unit (GPU). The data processor may be configured to implement model 22 according to machine readable instructions that define the topology of model 22 and data that specifies values for weights used in model 22. The data processor may be the same or different that the data processor on which model 20 exists on.

Figure 4:
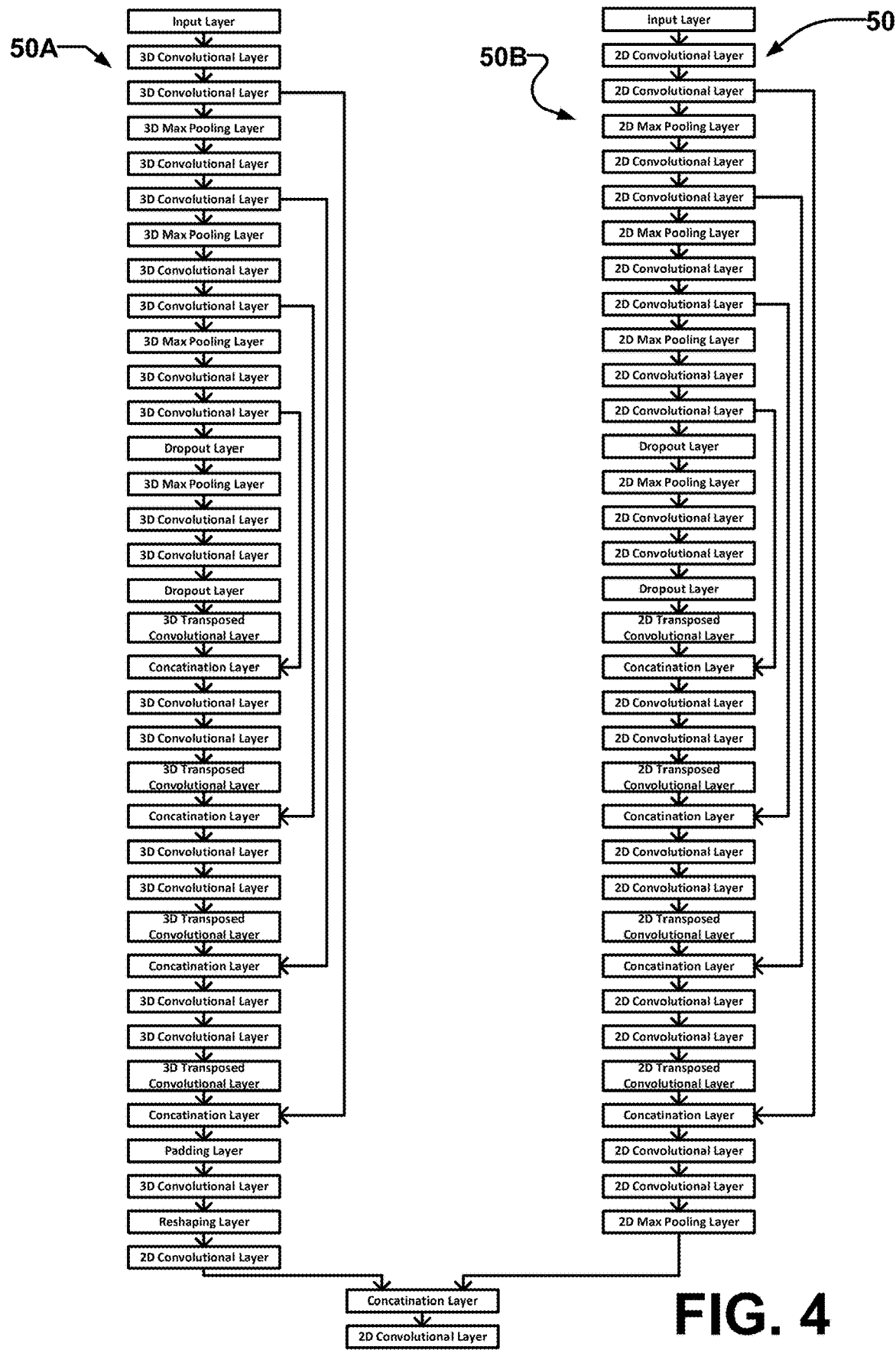
FIG. 4 is a block diagram of a machine learning model according to an example embodiment of the present technology.

FIG. 4 is a block diagram illustrating an example architecture 50 of model 22. Architecture 50 comprises a U-Net based convolutional neural network. Architecture 50 may comprise a plurality of branches (e.g. branches 50A and 50B). Each branch may comprise a down-sampling ("encoding") path and an up-sampling ("decoding") path. The down-sampling path may identify or locate larger features. The up-sampling path may up-sample the larger features (which are of lower resolution) and concatenate them with higher resolution features from a higher resolution layer. Preferably, both the encoder and the decoder have the same number of layers. Different branches may have the same or a different encoder-decoder depth. For example, each branch may, for example, have an encoder-decoder depth (i.e. the depth of an encoder or decoder individually in the branch) in the range of 2 to 10. In some embodiments at least one branch has an encoder-decoder depth of 4. Each branch may receive a different type of input. Two different inputs of the same type may be input into the same branch of the U-Net.

In a prototype embodiment, architecture 50 was implemented in Keras™ with a TensorFlow™ backend.

The inputs of model 22 may comprise data corresponding to a shear wave propagating through a desired tissue type and an image of the desired tissue region. The shear wave input comprises information regarding the temporal aspect of the shear wave (e.g. the travelling wave). Examples of the shear wave input include:

different states of the shear wave in time;

the real part and the imaginary part of the shear wave phasor;

the magnitude and the phase of the phasor (if magnitude and phase are used then the magnitude and the phase would be separated into different branches of architecture 50 and architecture 50 would comprise three branches in total due to the magnitude and the phase being different types of input);

etc.

The image of the desired tissue type may be an auxiliary input to assist model 22 since any good shear waves should be located within a particular tissue (e.g. within liver tissue). The image of the desired tissue type is preferably easily co-registerable with the shear wave imaging data. Preferably the image of the desired tissue type is from the same point of view as the shear wave imaging data.

Model 22 outputs an image or mask identifying pixels which represent good shear waves. Additionally, or alternatively, model 22 may output a numerical indicator indicating quality (overall quality or point by point quality) of the detected shear waves. In some embodiments model 22 outputs a binary indicator indicating the presence or absence of good shear waves.

In some embodiments branch 50A is configured to receive as input the displacement phasor of the shear wave. For example, branch 50A may receive three temporally equally spaced apart states of the phasor as input. Branch 50A may comprise a plurality of three-dimensional filters (e.g. convolutional filters).

Branch 50B may receive acquired image data of the tissue region as input. The acquired image data received by branch 50B is preferably easily registrable with the data received by branch 50A. Typically branch 50B receives b-mode ultrasound images as input however this is not necessary in all cases. In some embodiments branch 50B receives image data other than ultrasound image data. For example, branch 50B may receive MRI image data (e.g. T2 or T1 MRI images). In such example case, branch 50A receives magnetic resonance electrography (MRE) phasor data.

In some embodiments the convolutional layers of architecture 50 comprise a filter size and a stride that is sufficient to maintain the image size the same. In every up-sampling stage, the feature maps from the deconvolutional layer and the corresponding mirrored layer in the encoding path may be concatenated and then two convolutional layers may be used to reduce the number of feature maps. In the last stage of the branch 50A a 3D convolutional layer with no zero padding in the third dimension may be used to reduce the third dimension so it can be combined with the last stage maps of branch 50B. A convolutional layer with softmax activation may be used to obtain a final class-wise probability for each pixel (e.g. probability that each pixel corresponds to a good shear wave).

As described above there may be two (or more) inputs in the convolutional neural network (e.g. the phasor input and the image input). In one example embodiment the phasor input (e.g. for branch 50A) is created from a phasor corresponding to the shear wave with an example size of 128×128×3 and example pixel size of 1.1 mm. The image input (e.g. for branch 50B) may be an image (e.g. a corresponding b-mode image) with an example size of 256×256 and a pixel size of 0.55 mm. All inputs to model 22 may be normalized e.g. to a range of [−0.5, 0.5]. The 3 input channels of the phasor input (e.g. branch 50A) may be three equally spaced states of the phasor as described above. The three equally spaced states may, for example, be represented as:

$$\text{real}\left(e^{\frac{i2\pi}{3}k} \times \text{Phasor}\ (P)\right) \text{ with } k = 0,1,2.$$

In an example embodiment of model 22, 2000 sets of images (e.g. sets of shear wave images) collected from 15 different human patients with a Body Mass Index (BMI) range of 20-44 were used for training. The shear wave images were segmented manually into two categories (i.e. as good shear wave pixels and bad shear wave pixels) by a human trained to identify good shear waves. The adaptive moment estimator (e.g. commonly known as an Adam estimator) with cross-entropy loss function may be used for training model 22 and optimizing parameters of model 22. Data augmentation of the images may be used to increase the amount of data e.g. by flipping images horizontally, flipping images vertically, rotating images (e.g. in a range of 90 degrees) and zooming images (e.g. in a range of up to 0.2).

In another example embodiment of model 22, 20975 sets of images (e.g. sets of shear wave images) collected from 149 different human patients with a Body Mass Index (BMI) range of 20-44 were used for training. Additionally, 1200 images from four different phantoms (each with a different stiffness) were added to the training data.

As described above, images to be used for training of model 22 may be manually segmented by a human operator.

Once model 22 is trained, testing may be performed to validate model 22.

Figure 5:
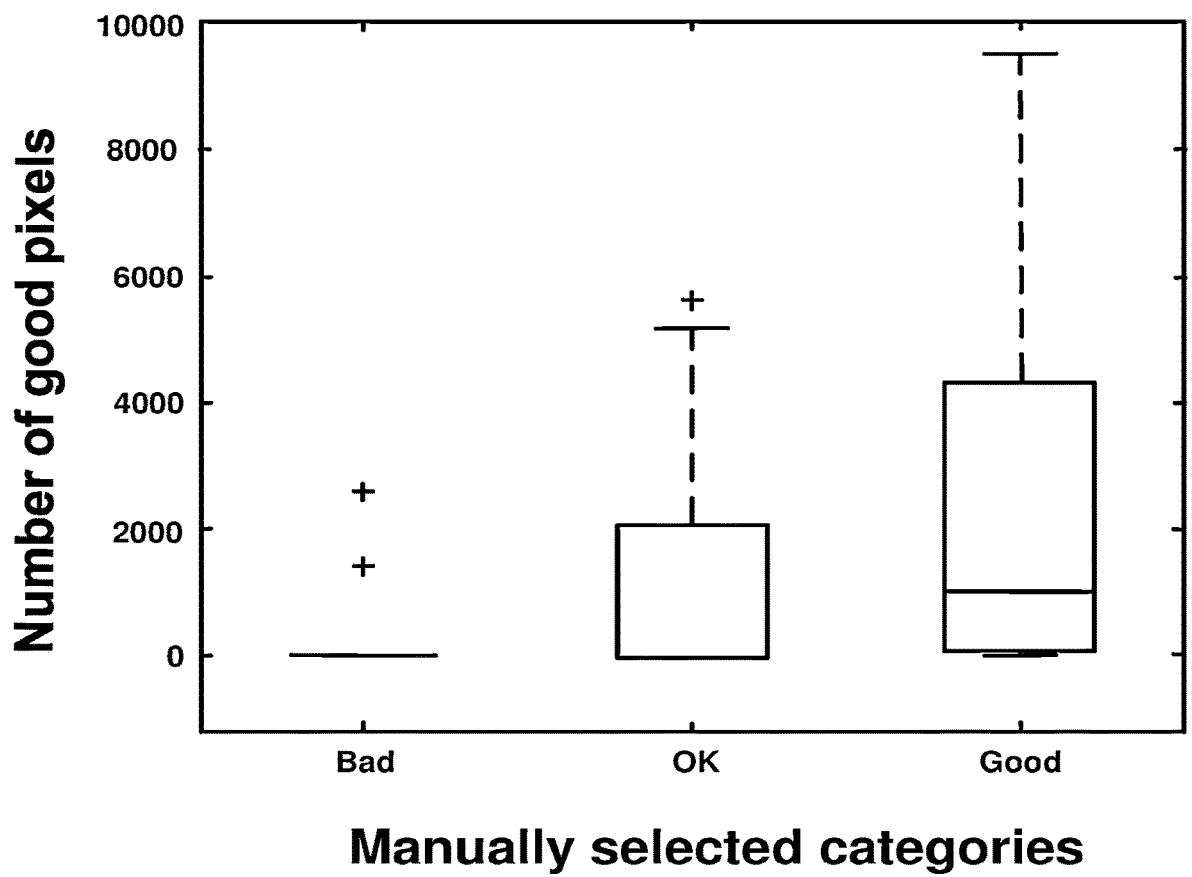
FIGS. 5 to 7 are graphical representations of data used to assess the quality of the machine learning model of FIG. 4.

For example, a set of images may be both manually categorized (e.g. into good, ok and bad shear waves) and input into model 22. FIG. 5 graphically illustrates an example comparison of good shear wave pixels identified by model 22 in the prototype embodiment relative to manually (e.g. by a human operator) identified categories.

As another example, images which are both manually (e.g. by a human operator) and automatically segmented (e.g. by model 22) may be compared by assessing accuracy (ACC), sensitivity (TPR), specificity (TNR) and balanced accuracy (BA) as defined below:

$$ACC = \frac{TP + TN}{P + N}, TPR = \frac{TP}{P}, TNR = \frac{TN}{N}, BA = \frac{TPR + TNR}{2}$$

where TP corresponds to a true positive, TN corresponds to a true negative, P corresponds to a condition positive (e.g. good shear wave) and N corresponds to a condition negative (e.g. a bad shear wave).

Figure 6:
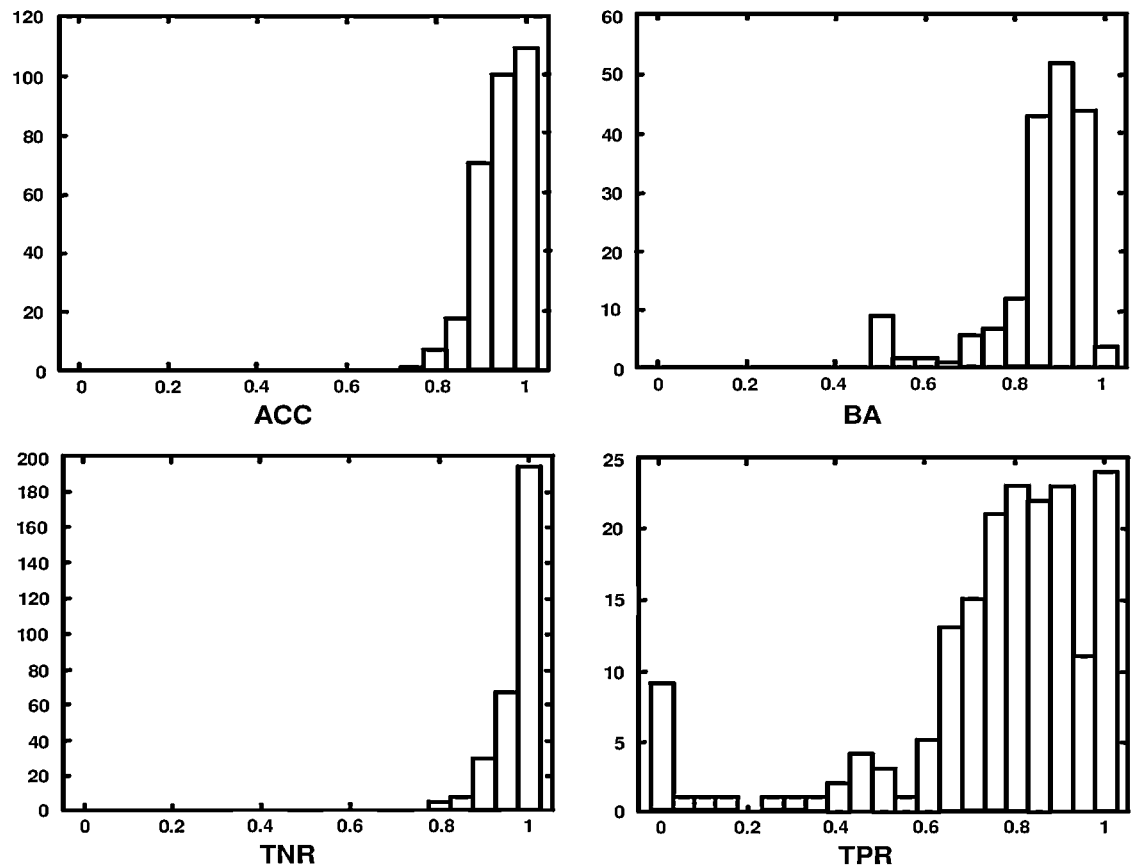
Figure 7:
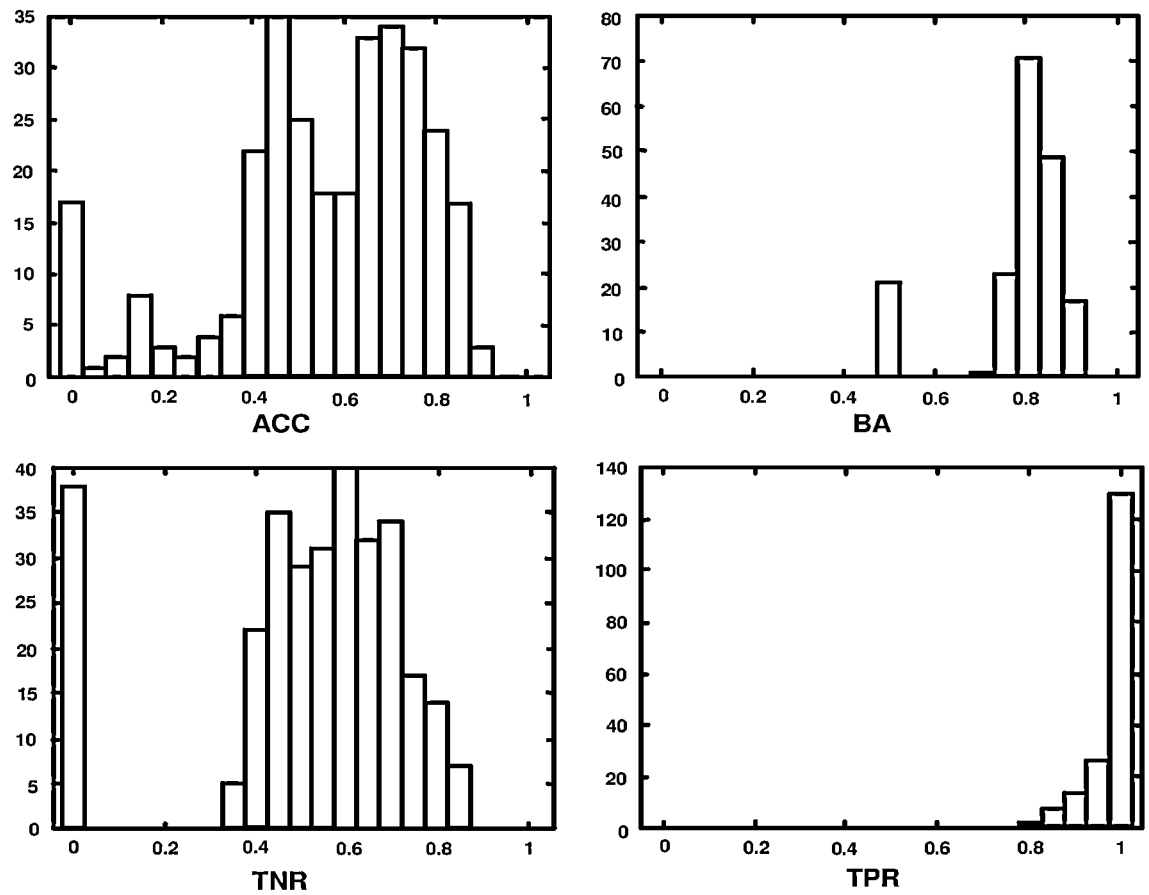

FIGS. 6 and 7 are example histograms of the above metrics for wave quality detection as may be performed by model 22 and an alternative pixel-based quality detection method (e.g. the alternative pixel-based quality detection method may comprise quality metrics such as signal to noise ratio or phasor fitting error as applied to individual pixels as opposed to observing the quality of a shear wave in several pixels simultaneously) respectively.

Quality Mask Generation

Two-dimensional or three-dimensional quality masks may be generated to identify which pixels of the acquired image data have one or more desirable characteristics as described elsewhere herein. For example, the generated quality masks may indicate: ultrasound signal-to-noise ratio, the ability of system 10 to track tissue displacement, the fitting of those displacements to the known frequencies of the input vibrations, shear wave presence, identification of a tissue type of interest, etc. An individual quality mask may be generated for each characteristic. Each of the generated masks may comprise pixels/voxels that comprise a probability (p) of the presence of a feature or characteristic of interest (f) or a binary label (feature present [p=1.0] or not [p=0.0]). A combined data quality mask Q, may be generated by combining two or more individual quality masks together. In some embodiments the individual quality masks are combined by assigning relative weights ($w_f$) to the different features of interest, summing their probabilities and then normalizing the sum as follows:

$$Q_i = \frac{\Sigma_f w_f p_{f,i}}{\Sigma_f w_f}$$

where $Q_i$ corresponds to the ith pixel/voxel in the mask and $f \in \{$liver tissue, shear wave quality, vessels$\}$.

The final combined quality mask may then be applied directly to input data as a way to determine which pixels of the input data to use for downstream processing (e.g. applying the combined quality mask as a weighting factor), as a binary label of good or bad data using a threshold Q value and/or the like.

In some embodiments two or more individual masks may be combined by performing a pixel wise logical AND operation.

The combined quality mask and/or one or more of the individual quality masks may be displayed to an operator (e.g. on display 16). For example:
- the only mask displayed may be a mask which highlights or identifies a desired tissue type (e.g. liver tissue);
- the only mask displayed may be a mask which identifies pixels corresponding to good shear waves;
- both a mask which highlights or identifies a desired tissue type (e.g. liver tissue) and a mask which identifies pixels corresponding to good shear waves may be displayed and their overlap is shown;
- only the overlapping portion(s) of a mask which highlights or identifies a desired tissue type (e.g. liver tissue) and a mask which identifies pixels corresponding to good shear waves may be displayed;
- any of the above where at least one of the masks is generated by combining multiple masks together;
- etc.

In some embodiments the mask(s) are displayed with a translucent overlay on a displayed ultrasound image which does not completely obscure the underlying features of the displayed image. This may, for example, provide the operator with real time visual feedback on the presence (or absence) of the desired tissue (e.g. liver tissue) in the image.

In some embodiments the shear wave quality mask is combined with an existing quality mask or mask which identifies a desired tissue type (as described above) and then similarly displayed as a translucent overlay but using a different colour from the other mask. In some such embodiments any overlapping portions of the two masks are displayed in a third colour. It is this area of overlap (that contains both the desired tissue (e.g. liver tissue) and good shear waves) that is ideally maximized during an image acquisition sequence. The area of overlap may, for example, be maximized by adjusting a position and/or orientation of transducer 14, adjusting a placement of exciter 15, adjusting one or more parameters of a control signal of exciter 15, adjusting one or more ultrasound imaging parameters, etc.

The quality metric (and any mask described herein) may be updated dynamically in real time.

Automatic ROI selection

Figure 8:
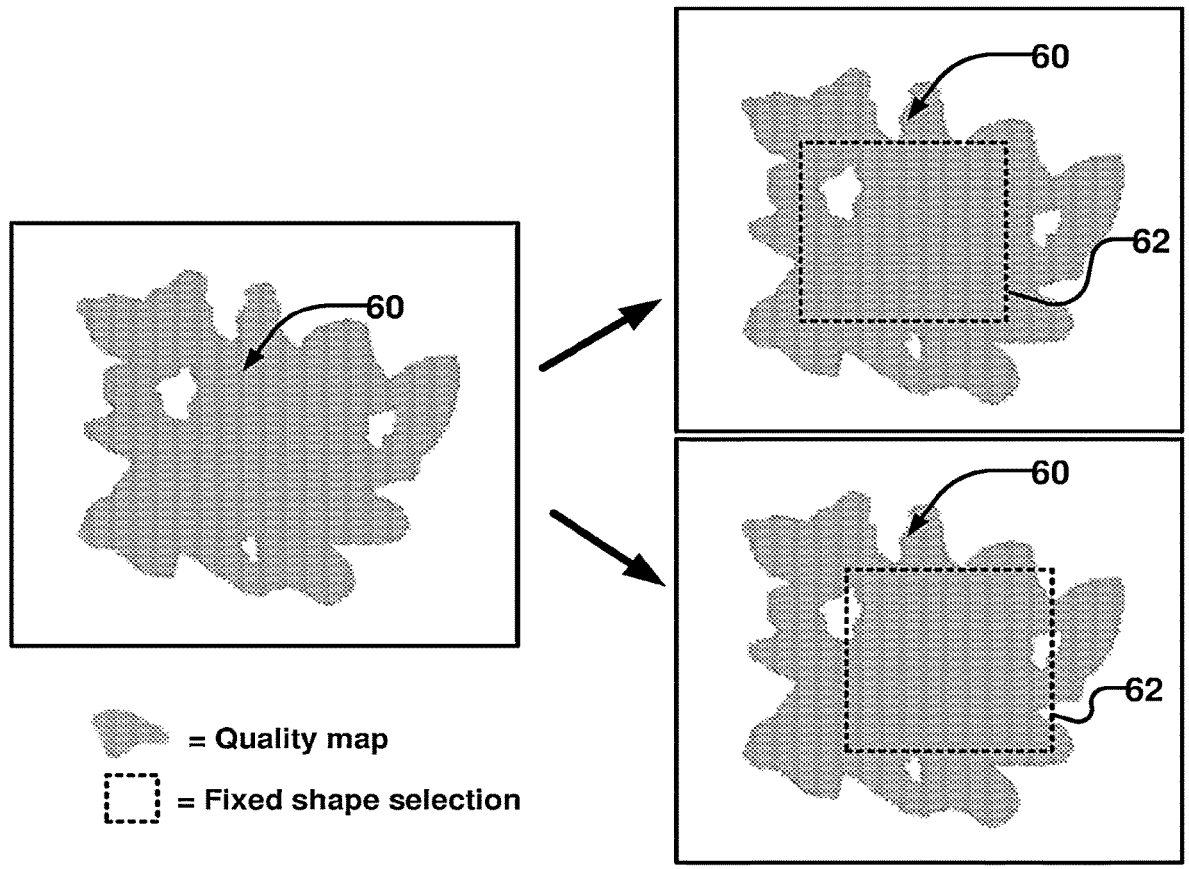
FIG. 8 is a schematic illustration of region of interest selection according to example embodiments of the present technology.

In order to accurately compute elasticity and attenuation measurements of the imaged tissue region, one or more of the quality mask described herein can also be cropped to a fixed two-dimensional or three-dimensional shape or region of interest (ROI) that contains the highest quality data. The shape of the ROI may be selected to maximize the total quality score in the fixed area (2D) or volume (3D). For example, the shape of the ROI may be selected to maximize the number of pixels which comprise both the desired tissue type (e.g. liver tissue) and good shear waves. The ROI may also take into account how contiguous the region is (whether there are "holes" or masked out sub-regions within the region) as well as the highest total quality score (e.g. a score representing how desirable the represented data is). For example, additional measures for continuous differentiability or Lipschitz continuity can be computed over the region and included in the overall score for an intended ROI. FIG. 8 schematically shows an example 2D quality map 60 which can have different placements for an ROI 62 (e.g. a fixed square) depending on weights assigned to the features as well as the contiguity requirement.

In some embodiments the fixed shape comprises a 2D square, rectangle, circle, ellipse, annular sector, etc. In some embodiments the fixed shape comprises a 3D cube, cuboid, sphere, ellipsoid, annular cylinder, etc.

In some embodiments placement of ROI 62 is dynamically varied in real time as image data is updated. In some embodiments controller 13 dynamically varies the position of ROI 62.

Example Application

In one example application of the technology described herein, a patient may want to assess the health of their liver. Exciter 15 may be positioned beneath the patient's abdomen. In some cases, the patient lies down on exciter 15. Exciter 15 may be controlled to induce shear waves into the patient's abdomen.

Ultrasound imaging data may be acquired with transducer 14. In some cases transducer 14 is moved relative to the patient's abdomen. As described elsewhere herein model 20 may segment the acquired ultrasound image data to identify liver tissue and model 22 may simultaneously assess the quality of the shear waves propagating through the patient.

Based on one or both of the segmentation and the shear wave quality assessment at least one visual indicator (e.g. a numerical indicator, a visual mask, etc.) of the quality of the acquired ultrasound imaging data may be displayed for the operator of system 10 (which in some cases is the patient themselves). If the quality of the acquired ultrasound imaging data is below a certain threshold (e.g. not enough pixels represent the desired tissue, don't have good quality shear waves, etc.) the operator of system 10 may adjust one or more parameters such as settings corresponding to ultrasound unit 12, a position or orientation of transducer 14, settings corresponding to exciter 15 (e.g. amplitude, frequency, etc.), positioning of the patient, etc. in an attempt to raise the quality of the acquired ultrasound imaging data.

In some cases a region of interest (ROI) is automatically selected and/or varied as described elsewhere herein.

In some cases system 10 (e.g. controller 13) processes the acquired ultrasound imaging data and shear wave data to determine an overall measure of elasticity of the imaged liver tissue. In some embodiments only the data corresponding to the ROI is processed. Based on the measure of elasticity a metric representing the overall health of the patient's liver may be computed.

The patient may later repeat the scan (e.g. in a week, a month, a couple of months, a year, etc.) to monitor for any changes in their liver health. The scan may, for example, be completed in a commercial setting (e.g. an imaging laboratory, Doctor's office, etc.) or in a residential setting (e.g. at the patient's residence).

The technology described herein has been described with reference to a desired tissue type. The present technology may be applied to any type of human or animal tissue. However, the inventors have determined that the tissue characteristics that can be measured by the present technology have particularly strong correlation to the health of liver tissue.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Software and other modules may reside on servers, workstations, personal computers, tablet computers and other devices suitable for the purposes described herein. Those skilled in the relevant art will appreciate that aspects of the system can be practiced with other communications, data processing, or computer system configurations, including: Internet appliances, hand-held devices (including personal digital assistants (PDAs)), wearable computers, all manner of cellular or mobile phones, multi-processor systems, microprocessor-based, network PCs, mini-computers, mainframe computers, and the like.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. All possible combinations of such features are contemplated by this disclosure even where such features are shown in different drawings and/or described in different sections or paragraphs. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for detecting presence of shear waves within a tissue of interest in a tissue region of a patient, the method comprising:
    exciting the tissue region of the patient with one or more exciters to induce propagation of shear waves within the tissue region by vibrating the tissue region with the one or more exciters;
    while exciting the tissue region, acquiring a plurality of ultrasound images of the tissue region with an ultrasonic transducer acoustically coupled to the patient;
    processing the acquired plurality of ultrasound images to determine characteristics of the shear waves;
    displaying at least some of the acquired plurality of ultrasound images on a display; and
    displaying on the display a visual indicator representing a measure measuring capture of the tissue of interest in the acquired plurality of ultrasound images within the tissue region and a quality measure of shear waves traveling through the tissue of interest, the visual indicator determined at least partially from:
        a first image mask indicating which pixels of the acquired plurality of ultrasound images represent the tissue of interest, the first image mask generated by inputting one or more of the acquired plurality of ultrasound images into a first machine learning model trained to identify the tissue of interest within one or more input ultrasound images; and
        a second image mask indicating which pixels of the acquired plurality of ultrasound images represent one or more shear waves to be used to determine an elasticity property of the tissue of interest, the second mask generated by inputting one or more of the acquired plurality of ultrasound images and shear wave data corresponding to the shear waves travelling through the tissue of interest into a second machine learning model trained to identify shear waves to be used to determine the elasticity property of the tissue of interest.

2. The method of claim 1 comprising cropping at least one of the visual indicator, the first image mask and the second image mask to a fixed two-dimensional or three-dimensional region of interest.

3. The method of claim 2 wherein cropping at least one of the visual indicator, the first image mask and the second image mask comprises maximizing within a crop region the number of pixels of the visual indicator, the first image mask or the second image mask which comprise both the tissue of interest and the one or more shear waves to be used to determine the elasticity property of the tissue of interest.

4. The method of claim 2 comprising dynamically varying the region of interest in real time as the acquired plurality of ultrasound images is updated.

5. The method of claim 1 comprising generating the first image mask and the second image mask concurrently.

6. The method of claim 1 wherein the visual indicator indicates at least one of ultrasound signal-to-noise ratio, ability to track tissue displacements, fitting of tissue displacements to known frequencies of input vibrations, shear wave presence and identification of tissue type.

7. The method of claim 6 wherein displaying the visual indicator comprises displaying a numeric representation.

8. The method of claim 6 wherein displaying the visual indicator comprises generating a third image mask, the third image mask generated by combing the first and second mask together.

9. The method of claim 8 comprising performing a pixel wise logical AND operation to combine the first image mask and the second image mask to yield the third image mask.

10. The method of claim 8 comprising displaying over the displayed at least some of the acquired plurality of ultrasound images at least one of the first image mask, the second image mask and the third image mask.

11. The method of claim 10 comprising displaying the first image mask in a first color, the second image mask in a second color different from the first color and the third image mask in a third color different from the first and second colors.

12. The method of claim 1 wherein the first machine learning model is trained to detect the tissue of interest based on boundaries of the tissue.

13. The method of claim 12 wherein the first machine learning model is trained to segment pixels of the one or more ultrasound images inputted into the first machine learning model into at least a first group corresponding to the tissue of interest and a second group corresponding to tissue other than the tissue of interest.

14. The method of claim 13 wherein the first machine learning model comprises a convolutional neural network.

15. The method of claim 14 wherein the first machine learning model comprises a U-Net convolutional neural network.

16. The method of claim 1 wherein the first image mask comprises a binary mask.

17. The method of claim 1 wherein the first image mask comprises pixel values representing a probability that the corresponding pixels of the acquired plurality of ultrasound images represent the tissue of interest.

18. The method of claim 1 wherein the second machine learning model comprises a convolutional neural network.

19. The method of claim 18 wherein the second machine learning model comprises a U-Net convolutional neural network.

20. The method of claim 19 wherein the second machine learning model comprises a first branch configured to receive as input the shear wave data and a second branch configured to receive as input the one or more ultrasound images inputted into the second machine learning model.

21. The method of claim 1 wherein the shear wave data comprises at least one of:
different states of the shear waves in time;
a real part and an imaginary part of a phasor representing the shear waves; and
a magnitude and phase of the phasor.

22. The method of claim 1 wherein the tissue of interest comprises liver tissue.

23. A method for detecting presence of shear waves within liver tissue of a patient, the method comprising:
exciting an abdominal region of the patient with one or more exciters to induce propagation of shear waves within the liver tissue by vibrating the abdominal region with the one or more exciters;
while exciting the abdominal region, acquiring a plurality of ultrasound images of the abdominal region with an ultrasonic transducer acoustically coupled to the patient;
processing the acquired plurality of ultrasound images to determine characteristics of the shear waves;
displaying at least some of the acquired plurality of ultrasound images on a display; and
displaying on the display a visual indicator representing a measure measuring capture of the liver tissue in the acquired plurality of ultrasound images within the abdominal region and a quality measure of shear waves traveling through the liver tissue, the visual indicator determined at least partially from:
a first image mask indicating which pixels of the acquired plurality of ultrasound images represent the liver tissue, the first image mask generated by inputting one or more of the acquired plurality of ultrasound images into a first machine learning model trained to segment pixels of the one or more ultrasound images inputted into the first machine learning model into at least a first group corresponding to liver tissue and a second group corresponding to tissue other than liver tissue; and
a second image mask indicating which pixels of the acquired plurality of ultrasound images represent one or more shear waves to be used to determine an elasticity property of the liver tissue, the second mask generated by inputting one or more of the acquired plurality of ultrasound images and shear wave data corresponding to the shear waves travelling through the liver tissue into a second machine learning model trained to identify shear waves to be used in a method of elastography of liver tissue to determine the elasticity property of the liver tissue.

* * * * *